United States Patent [19]
Andelman

[11] Patent Number: 5,200,068
[45] Date of Patent: Apr. 6, 1993

[54] CONTROLLED CHARGE CHROMATOGRAPHY SYSTEM

[76] Inventor: Marc D. Andelman, 6 Nadine Rd., Framingham, Mass. 01701

[21] Appl. No.: 819,828

[22] Filed: Jan. 13, 1992

Related U.S. Application Data

[63] Continuation-in-part of Ser. No. 792,902, Nov. 15, 1991, which is a continuation of Ser. No. 512,970, Apr. 23, 1990, abandoned.

[51] Int. Cl.$^5$ ............................................. B01D 15/08
[52] U.S. Cl. ................................. 210/198.2; 210/243; 210/541; 204/180.1; 204/299 R
[58] Field of Search ..................... 204/180.1, 299 R; 210/635, 656, 747, 198.2, 243, 541

[56] References Cited

U.S. PATENT DOCUMENTS

| | | | |
|---|---|---|---|
| 2,555,487 | 6/1951 | Haugaard | 204/299 R |
| 2,741,591 | 4/1956 | Dewey | 204/299 R |
| 2,853,448 | 9/1958 | Heiskell | 204/180.1 |
| 3,324,026 | 6/1967 | Waterman | 204/299 R |
| 3,450,624 | 6/1969 | Natelson | 204/299 R |
| 3,451,918 | 6/1969 | Kolin | 204/299 R |
| 3,640,813 | 2/1972 | Nerenberg | 210/198.2 |
| 3,846,274 | 11/1974 | Gifford | 204/299 R |
| 3,847,773 | 11/1974 | Snyder | 204/299 R |
| 4,049,534 | 9/1977 | Posner | 204/299 R |
| 4,057,482 | 11/1977 | Candor | 204/299 R |
| 4,560,445 | 12/1985 | Hoover | 204/30 |
| 4,743,373 | 5/1988 | Rai | 210/198.2 |
| 4,769,191 | 9/1988 | Newman | 204/403 |

OTHER PUBLICATIONS

Bassler & Hartwick, "Electrically Conductive Stationary Phases for HPLC from Aichie Meeting in San Francisco, Calif.", Abstract, Nov. 1989.
Antrim et al., "Electrochromatrography-A Prelimary Study of the Effect of Applied Potential on a Carbonaceous Chromatographic Column", Anal. Chim. Acta., 1984, p. 283.
Blaedel et al., "Continuous Quantitative Electrolysis", Anal. Chem., Jun. 1964, pp. 1245-1251, vol. 36, No. 7.
Strohl et al., "A Packed Graphite Cell for Thin-Layer Chromatography", Analytical Letters 2(8), 423-431 (1969).
Fujinaga, T., "Electrolytic Chromatrography and Coulometric Detection with the Column Electrode", Pure Applied Chemistry, 25 (1971) pp. 709-726.
Hem et al., "Modified Graphites for Chelation and Ion Exchange", Analytical Chemistry, Dec. 1978, pp. 1954-1959, vol. 50, No. 14.
Stoner et al., "Absorption of Blood Proteins on Metals Using Capacitance Techniques", Journal of Physical Chemistry, Mar. 5, 1970, pp. 1088-1094, vol. 74, No. 5.
"KF for Electro Double Layer Capacitors", Toyobo Co Bulletin, PCF110 Sep. 1984 Naldrop, Science vol 247, Jan. 12, 1990, p. 161.

Primary Examiner—Ernest G. Therkorn
Attorney, Agent, or Firm—Richard P. Crowley

[57] ABSTRACT

A controlled charge chromatography column for the purification of a fluid-containing material, which column comprises a chromatographic column having an inlet for the introduction of a fluid to be purified and an outlet for the discharge of the purified fluid, and one or more concentrated materials and a flow-through capacitor disposed within the column between the inlet and outlet, the flow-through capacitor means comprising a plurality of spirally wound or stacked washer layers to include a first electrically conductive backing layer, such as of graphite, and a first high surface area conductive layer secured to the backing layer, such as composed of porous carbon fibers and a non-conductive, porous spacer layer to electrically insulate the backing and conductive layer and to permit the flow of material therethrough, the flow-through capacitor to be connected to a DC power source to charge the respective conductive layers with different polarities whereby a fluid containing material through the colum is purified by the electrically conductive stationary phase and the retention thereof onto the high surface area layer and permitting for example the purification of solutions of liquids, such as salt, and providing for the recovery of a purified liquid.

14 Claims, 3 Drawing Sheets

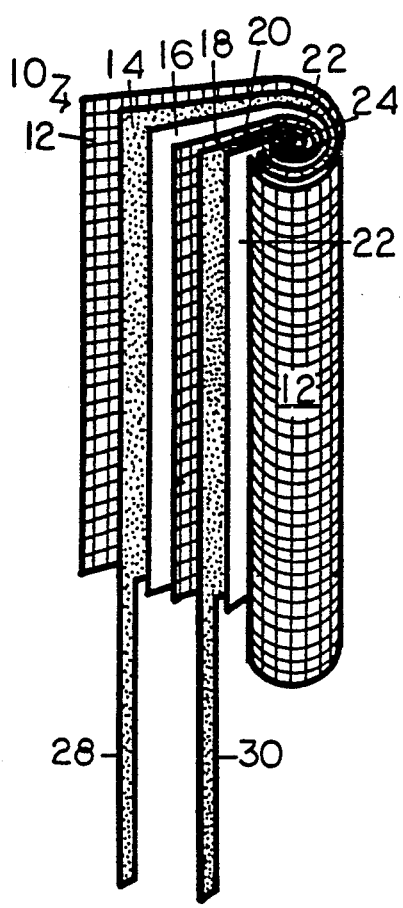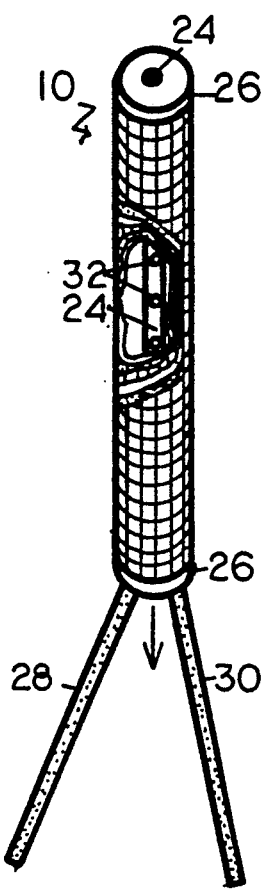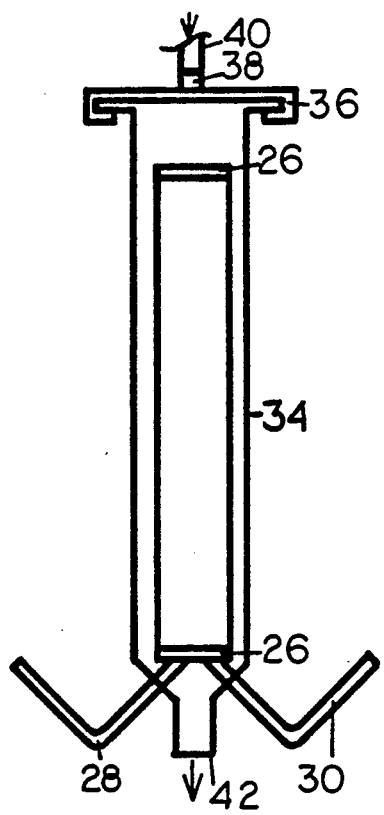
FIG.1  FIG.2  FIG.3
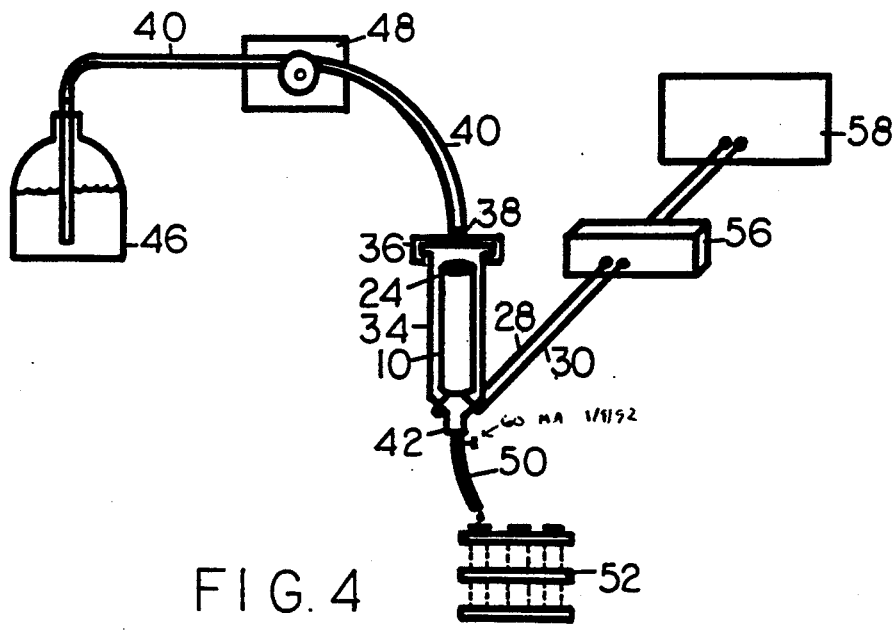
FIG.4

CONTROLLED CHARGE CHROMATOGRAPHY SYSTEM

REFERENCE TO PRIOR APPLICATIONS

This application is a continuation-in-part patent application of allowed U.S. Ser. No. 07/792,902 filed Nov. 15, 1991 which is a continuation patent application of U.S. Ser. No. 07/512,970, filed Apr. 23, 1990, now abandoned.

BACKGROUND OF THE INVENTION

Chromatographic columns, particularly liquid chromatographic columns, have provided for the employment of an electrically conductive, stationary solid phase, and the preferential interaction of solutes in a fluid to be chromatographically separated with the solid, stationary phase, such as set forth in "Electrically Conductive Stationary Phases for HPLC"[1] issued by Barbara Bassler and Richard Hartwick, Abstract from the AICHE Meeting, San Francisco, Calif., Nov. 5-10, 1989, and in "Electrochromatography—A Preliminary Study of the Effect of Applied Potential On A Carbonaceous Chromatographic Column"[2], by Robert Antrim, Robert Scherrer and Alexander Yacynych, *Anal. Chim. Acta.*, 164 (1984) 283. The above references describe an electron rich, porous, graphitic, carbon, stationary phase to act as a controlled potential surface to affect the resolution of solutes to be chromatographed in both polar and non-polar solvents. In such chromatographic columns as HPLC, the conductive packing is employed as one electrode and the surrounding metal tube of the column as the other electrode. These columns do not act as capacitors, since the voltage drop is generally entirely across the metal tube and insignificant across the claimed controlled potential surface to be modulated, so that little electrostatic absorption occurs.

In addition, electrically conductive stationary phases have been employed to deposit and strip solutes via electrolysis, see for example, "Continuous Quantitative Electrolysis"[3], W. J. Blaedel and J. H. Strohl, *Anal. Chem.*, Vol. 36, No. 7, June, 1964; "A Packed Graphite Cell For Thin Layer Electrochemistry"[4], John Strohl and Thomas Polutanovich, *Analytical Letters*, 2(8), pp. 423-431 (1969); "Electrolytic Chromatography and Coulometric Detection With the Column Electrode"[5], Taitiro Fujinaga, *Pure Applied Chemistry*, 25 (1971) pp. 709-726; and "Modified Graphites for Chelation and Ion Exchange"[6], James Hern and John H. Strohl, *Analytical Chemistry*, Vol. 50, No. 14, December, 1978. In addition, capacitance techniques have been employed for the absorption of blood proteins on metals, as set forth by G. Stoner and S. Srinivasan, "Absorbtion of Blood Proteins on Metals Using Capacitance Techniques"[7], *Journal of Physical Chemistry*, Vol. 74, No. 5, pp. 1088-1094, Mar. 5, 1970. While electrolysis devices have been used to purify solutions, the devices affect purification by deposition and stripping electrochemically the material and not by electrostatic absorption.

U.S. Pat. No. 4,769,191, issued Sep. 6, 1988, describes an anode electrode of an electrolytic capacitor having a biochemically active layer embedded in the pores of the electrodes and that the electrodes change electrical properties by the presence of the chemical layers. This patent discloses using a biochemical layer and wherein analyte molecules replace other molecules from the biochemically active layer to effect the change in the dielectric properties of the electrodes, and this charge is employed to measure the concentration of analyte molecules.

None of the above prior art references describe a device which effects absorption or resolution of solutes to be chromatographed via a high capacitance, combined with a flow-through configuration to allow the capacitor to function as a chromatographic system. It is desirable to provide for controlled charge chromatography system and method which employs a flow-through capacitor of high surface area material for both anode and cathode, to provide for a high efficiency, effective purifying system to modulate the absorption and/or resolution of ions and non-ionic solutes in polar and non-polar solvents.

SUMMARY OF THE INVENTION

The present invention relates to a controlled charge purification chromatography system and method, and more particularly relates to a chromatography system and method employing a flow-through capacitor of high electrical capacitance and high surface area absorption capacity.

A controlled charge chromatography system and method has been discovered which provides for the purification of solutes particularly in liquids containing both non-polar and polar materials, and which column comprises a column having an inlet for the introduction of the fluid to be purified and an outlet for the discharge of the purified fluid and one or more concentrated ionic materials. The controlled charge chromatographic column would also include a flow-through capacitor means disposed within the column between the inlet and the outlet so as to permit the flow of the fluid through the flow-through capacitor means, with the flow-through capacitor means adapted to be connected to a DC power source to place charges on the film or layers in the capacitor. The flow-through capacitor may comprise a wide variety of configurations, such as for example a spirally wound capacitor. Such a spirally wound, flow-through capacitor would comprise a plurality of spaced apart layers with the layers generally axially aligned with the axis of the column, and the layers including a first non-conductive, porous spacer layer to define a flow channel to permit the flow of the feed fluid therethrough. For example, the spacer material may comprise a porous, inert-type material, such as woven, open space, synthetic material, such as nylon or fiberglass screen-like spacing material. A first electrically conductive backing layer may be composed of any electrically conductive material, such as a metal film for example of aluminum and/or more particularly of electrically conductive graphite. A first high surface area conductive layer material is secured or placed adjacent to the electrically conductive backing layer providing a very high surface area by virtue of a highly porous structure, and more particularly would comprise, for example, a compressed, activated carbon which is porous, or even more particularly, an activated carbon woven fibrous layer. The conductive layer may for example be wound in a spiral formation with the porous spacer material between the respective layers with six layers wound so as to provide for separate and opposite charges on two separate spirally wound backing layers.

Electrical leads may be connected to the first and second electrically conductive backing layers to a DC power source so that layers may be formed integrally with the backing layers. Generally, the flow-through capacitor may be prepared in spiral wound form by winding the respective layers about a central hollow perforated tube from inside to outside composed of a spacer layer, a backing layer, a high surface layer, a spacer layer, a backing layer and a high surface layer about a central plastic tube containing perforations therein and then sealed at the end by a resin, such as a thermoset epoxy resin, so as to provide for the introduction of the fluid material through the side of the spirally wound device, through the successive layers, and the purified fluid and the one or more ionic materials concentrated by the flow-through capacitor to be discharged from the other end of the central tube.

The controlled charge ionic purification chromatography system would thus include the chromatographic column containing the flow-through capacitor with a source of fluid, such as a liquid containing ionic materials, a pump means to pump or otherwise introduce the liquid material into the inlet of the chromatographic column, the column typically containing a cartridge-type flow-through capacitor, with the leads of the flow-through capacitor extending out of the column and secured to a DC power source, optionally to a logic device to program voltage on/off cycles, voltage gradients and reversal of polarity and otherwise to control electrically the capacitor and wherein the system also includes a collection disposed adjacent the outlet of the column whereby the purified material or the various eluting, concentrated ionic materials may be separately collected.

The method of the invention comprises flowing a fluid containing ionic material, either polar or non-polar solvents, through a flow-through capacitor in which the capacitor is a high capacitance, for example, over 1000 farads capacitance, and further which includes a high surface area conductive layer secured to a backing and separated by a spacing layer from the adjacent high surface area layer and backing so as to increase the retention capacity and electrical capacitance of the capacitor. The charge on the capacitor is controlled so as to attract and hold charged molecules in the fluid by virtue of the charge-holding ability implicit in the capacitance of the capacitor thereby providing for a method of purifying and/or analyzing charged molecules, for example, in a solution by modifying the concentration of the fluid as it passes through the flow-through capacitor.

The flow-through capacitor of the invention may be employed in various designs provided that the solution can flow-through or across the charged metal plates or layers, or ionic plates in the case of electrolytic capacitors, wherein the flow-through capacitor comprises a porous spacer layer to permit the flow of the fluid, an electrically conductive layer and a high surface area electrically conductive layer adjacent or in electrical communication with the backing layer. The flow-through capacitor may comprise a film capacitor wherein the fluid is passed between a pair of metal electrodes having an insulating, dielectric film passed between the electrodes. Some of the film-type capacitors provide for a low capacitance which may be useful for analytical purposes where small amounts of analyte is desired. However, such film capacitors have an inherently low capacitance, and therefore, a low charge holding ability. Electrolytic capacitors may also be employed and employ certain metals, such as aluminum and tantalum, which metals tend to form oxide layers which adhere tightly to the metal and which are also good insulators and constitute very thin insulating layers. The capacitance increases with the thinness of dielectric layers. Therefore, these thin oxide layers provide exceptional capacitance. In electrolytic capacitors one of the two metal plates typical of other capacitors has been replaced by an ionic solution which forms intimate contact with the oxide and reacts with the metal to form the oxide itself. Electrolytic capacitors typically use aluminum or tantalum. Aluminum tends to be soluble outside of a barrow pH frame and is readily attacked by halides and therefore is easily corroded, but its cost is low, while tantalum has a non-soluble oxide layer which is stable over a broad pH range and is also immune to corrosion. Hence, the electrolytic capacitors have a relatively high capacitance. However, the amount of capacitance needed to purify even a dilute solution is extremely large, therefore electrolytic capacitors define typical uses for purifying high purity water or protein purification where the feed stream is relatively dilute with the ionic concentrations.

The flow-through, double layer capacitor of the invention avoids the problems associated with typical thin film or electrolytic capacitors, since capacitance is inversely proportioned to the dielectric thickness and directly proportioned to electrode surface area. The flow-through capacitor of the invention employs a conductive layer with a high surface area electrically conductive material layer. In one preferred embodiment, the high surface electrically conductive layer may comprise a porous carbon fiber layer typically a porous, woven, flexible fiber cloth layer in contact with an electrically conductive backing layer, and more particularly of a flexible graphite layer which is highly electrically conductive. The high surface area electrically conductive layer may also comprise palladium or platinum black. Activated carbon may also be employed; however, in granular form, activated carbon is not a good electrical conductor unless it is in a compressed, porous form; however, compressing reduces the porosity.

One preferred embodiment of the invention comprises an active carbon fiber woven layer which provides for electrical conductivity and high porosity, although any other material which is highly electrically conductive and which has micropores can be employed for the high surface active area. For example, capacitors made with Toyobo Co. activated carbon KF cloth have 1000× the charge delivery as electrolytics (see "KF for Electro Double Layer Capacitors"[9], Toyobo Co. Bulletin, PCF 110).

For example, one material which may be employed as the high surface area layer comprises a material known as azite, a black ceramic-like substance, which is highly porous and very strong and yet electrically conductive and is composed of a synthetic carbon polymer whose structure is flat with holes (pores) (see Science[10], Jan. 12, 1990). In addition, it may be desirable to provide for a chemical modification of the high surface area electrically conductive layer by the employment of adsorbing molecules thereon to alter the electrical characteristics, such as for example, adsorbing an aromatic molecule that contains a charge group onto the carbon cloth material layer which chemical modification of the surface active area may act as an ion exchanger. Azite material consists of micropores which provide superior capacitance properties due to the elimination of one diffusion barrier, that is, macroporous and microporous layers, and is easy to fabricate. Azite material provides for a three dimensional structure and may thus be used alone in connection with merely a non-porous dielectric spacer to provide a flow-through capacitor. In addition, since the three dimensional structure of azite is flat with holes, convective flow right through the pores of the material allows a faster method of purification than other materials, such as activated carbon and platinum black, where the porosity is on the surface, and slower processes of electrodiffusion set a limit on the speed of separation.

In one embodiment of a flow-through capacitor of the invention, a spirally wound plurality of layers is adapted to be wound around a hollow central core, the central core acting as the inlet and outlet of the chromatographic column and the central core having a plurality of holes through its length so as to permit the fluid to be separated or purified and to the non-conductive, porous spacer layer in the flow-through capacitor. The flow path may be down through the central layer or from the outside of the flow-through cartridge which is placed in the chromatographic column. Generally, the flow-through capacitor may be sealed at each end and has extending leads which are adapted to be connected to a DC-controlled power supply. The cartridge is formed by rolling up the porous spacer layer, the conductive backing layer, the conductive high surface layer, together with another conductive, porous spacer layer, a second conductive backing layer and the second conductive high surface area layer all about the central tube.

The invention comprises a flow-through capacitor for use in a chromatographic system for the purification of a liquid-containing material.

In another embodiment, the flow-through capacitor of the invention may comprise a plurality of stacked washers or disks secured about a central, non-conductive tube or support means with the washer ends sealed. The central tube means may be porous or have holes punched therein or be a rod having a longitudinal groove(s) for liquid flow.

The stacked washers comprise in series a first nonconductive spacer washer, for example, of a nonwoven, spun-bonded, polymeric, fibrous material, like polypropylene or polyester, a second high surface area conductive washer, for example, a relatively thick layer, e.g. 25 to 200 mils, composed of extruded, activated carbon, conductive polymers, platinum black, compressed bucky balls, etc. and a first conductive backing washer generally a relatively thin, flexible sheet material, e.g. 1 to 5 mils, of graphite foil or a conductive metal, like silver or titanium, on which platinum black is electrodeposited to enhance surface area. Optionally, but preferably, the conductive backing washer has a plurality of holes to permit liquid flow through. The washers are arranged in sequence and stacked about the central tube and secured together in an compressed, contacting arrangements by the pressure of threaded end caps or by threaded rods on each side or by other means. The number of stacked washer units can vary as desired, for example, 10 to 40. Electrical anode and cathode leads from a DC power source are connected to the first and other electrically conductive washers. In one method of connection, notches may be cut in the outside periphery of each conductive backing layer and then opposite rigid electrodes with attending matching tabs secured to each side of the stacked washers with the tabs in electrical contact with the notches of the conductive backing washer.

In another means of electrical connection, the conductive backing washers are made in attached pairs of washers with a short, flexible extension between the washers, so that the extension forms an outwardly extending, bulging, V-shaped, peripheral tab on assembly of the stacked washers, for example, of flexible graphite foil. The electrodes on each side are then placed in contact with the alternate side extending tabs.

The flow-through capacitor may have threaded plastic end caps which are threadably secured to the threaded ends of the central tube. The stacked washer flow-through capacitor is then placed within a cartridge holder, such as a standard filter cartridge, with one end of the capacitor sealed by a rubber washer against the outlet of the cartridge. The cartridge would have combination anode and cathode rods, e.g. graphite, extending therethrough and connected to the alternating conductive backing washers. The cartridge includes an inlet for the introduction of a fluid about the capacitor and with the fluid flow from the outside inwardly while subject to a controlled electrical charge. The liquid is then withdrawn from the central tube to the outlet.

The one end of the tab support means may be sealed so that the discharge of purified liquid is from the one open end to the outlet, or the tab supports may be open to each end and each end sealed within the cartridge and purified liquid collected from each end.

The controlled charge chromatography system may be employed for the separation of a wide variety of fluids and more particularly, any solute, solvent or liquid system that wants to be concentrated or purified by resolving into separate species. The solvent can be polar, such as water, or non-polar, such as an aromatic, which fluid contains material which has selectivity for the solid phase and which can be modulated by controlling the charge of the solid phase, that is, the high surface area layer. For example, the solution may be of deionized water with resolved bands of ionic species, such as sodium chloride or other salts, and also any other types of molecules, organic, inorganic or biological. The invention will be disclosed for the purposes of illustration in connection with the separation of ionic liquid solutes; however, the system and method may be advantageously employed and used in the separation of other fluids, such as, but not limited to: non-ionic solutes, like hydrophobic solutes, or other fluids which contain one or more components which interact or are affected by electrically conductive surfaces, for example, liquids containing DNA, viruses, bacteria, cells, colloids or mixtures thereof. The flow-through capacitor permits the control of the charge on the stationary phase as the high surface area phase of the flow-through capacitor.

The invention will be described for the purposes of illustration only in connection with certain embodiments; however, it is recognized that those persons skilled in the art may make various modifications, changes, improvements and additions to the preferred embodiments or illustrated embodiments, all without departing from the spirit and scope of the invention.

BRIEF DESCRIPTION OF THE DRAWINGS

FIG. 1 is an illustrative, schematic, partially exploded view of the flow-through capacitor of the invention;

FIG. 2 is a schematic, illustrative view of the completed flow-through capacitor of the invention;

FIG. 3 is a schematic, illustration of a chromatographic column employing the flow-through capacitor of the invention;

FIG. 4 is a schematic illustration of a controlled charge ionic purification chromatography system and method of the invention.

DESCRIPTION OF THE EMBODIMENTS

Figures 5, 6:
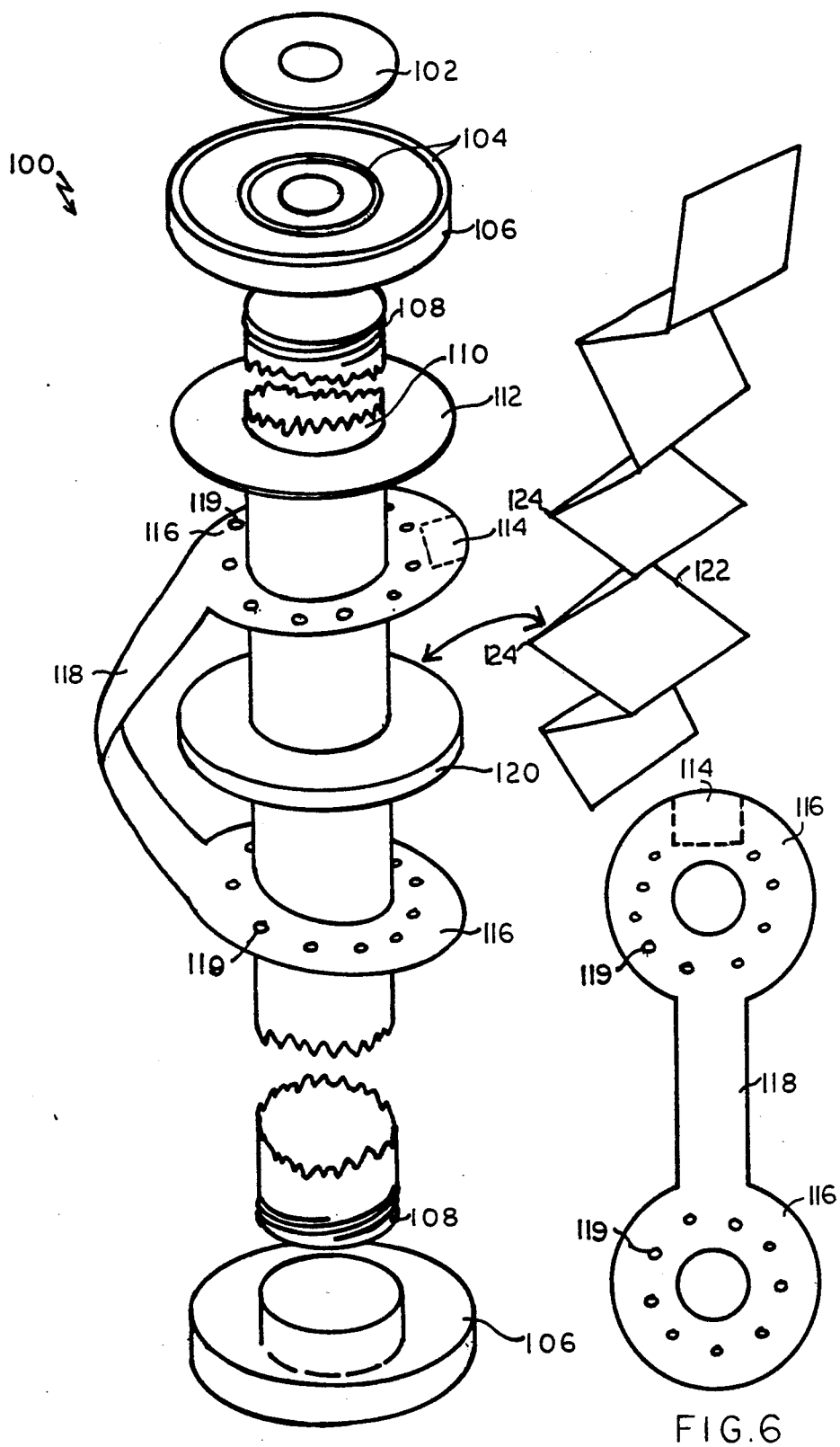
FIG. 5 is a schematic illustrative, exploded view of a stacked washer flow-through capacitor of the invention.
FIG. 6 is a top plan view of the conducting backing washer used in FIG. 5.

With particular reference to FIGS. 1 and 2, there is shown in FIG. 1 an exploded view of the flow-through capacitor of the invention 10 comprised of a plurality of layers wound about a central plastic tubing 24 having a plurality of perforations 32 therein extending down its length and having a one end which serves an inlet for a fluid to be purified and an other end which serves as an outlet for the discharge of the purified fluid and the ionic species. Layers 12 and 18 which may be the same or different from a non-conductive porous spacer sheet material having a thickness for example of about 50 mils to 120 mils, and more particularly, a layer of nylon woven cloth which forms a non-conductive spacer material between the anode and the cathode. Layers 14 and 20 comprise a conductive backing layer which optionally may have holes punched therein to improve flow properties and which may include horizontal leaves extending therefrom to act as leads 28 and 30 for connection to a power source. For example, the conductive backing may comprise Union Carbide's Graphoil ® brand 5 mils thick graphite foil with pin holes punched therethrough. Layers 16 and 22 are comprised of a high surface area conductive material, and more particularly in the illustrated embodiment, and activated carbon woven fiber cloth to form a charge-holding, conductive high surface area (for example cloth ANF #62 from Toyobo of Japan).

FIG. 2 is a schematic illustration of the flow-through capacitor wherein the layers have been wrapped around the central core 24 wherein both ends are sealed with an epoxy resin 26 leaving open the inlet of the tube 24 and the outlet. FIG. 2 illustrates a partial sectional view that the inner core tube 24 has a series of holes 32 therein, for example, 16, 1 mm diameter holes, 1/10" apart, on a 3/16" outside diameter tubing as the core. In another embodiment, the capacitor may have no epoxy seals, and a solid tube for a central core, so the flow is between the layers. The capacitor may have the top end of the hollow tube sealed shut so that the direction of flow is through the sides of the device, through the successive layers, and then out the open end of the inner hollow tube.

FIG. 3 is an illustration of chromatographic column 34 containing the flow-through capacitor 10 disposed therein and generally axially aligned with the axis of the column 34, the column having an end cap 36, an inlet 38 and connected to a tubing 40 for the introduction of a fluid material to be purified, the end cap gasketed to a defined pressure, for example, 100 psi, and the column 34 having an outlet 42. Extending from the column 34 are the conductive leads 28 and 30 which have epoxy seals where the outlet tubing 50 and the Graphoil leads 28 and 30 come through column 34. For example, the column 34 may comprise a transparent, plastic, polypropylene, syringe-type barrel.

FIG. 4 is a schematic illustration of a controlled charge purification chromatography system and includes a source of fluid, such as a solution source 46, inlet tubing 40 which passes through a pump 48 to connect the fluid into the inlet 38 of the end cap 36 of the chromatographic column 34 which contains the flow-through capacitor 10 wherein the leads 28 and 30 from the capacitor 10 are connected to an electric control system 56 which programs and controls the voltage, the off/on cycles, voltage gradients and permits reversal of polarity and otherwise controls the electric power to the flow-through capacitor through a 24-volt DC power supply 58. The outlet from the column 34 is through outlet 42 through a tube 50 which directs the material or the elution to a rotating-type fraction collector schematically illustrated as 52. The outlet 42 may have an on/off fluid control valve.

The chromatographic system as illustrated in FIG. 4 may be employed to provide for the purification of a variety of solutions containing ionic material, and for example, the purification of a 0.01 molar sodium chloride aqueous solution from feed 46 which is fed by pump 48 through tubing 40 into the inlet 38 of the end 36 to the column 34 and hence, through 24 into the flow-through capacitor 10 which has a controlled charge thereon of about 2 volts. The sodium chloride feed solution is purified to a $1 \times 10^{-4}$ molar at a flow rate of 0.23 ml/minute from the outlet 42 through control valve 60 into the tubing 50 into the fraction collector 52, while 2 volts are also supplied to the DC power supply through logic 56 to leads 28 and 30 to provide a flow-through capacitor. The purified sodium chloride solution was recovered simply by shorting the leads 28 and 30. In other examples, much larger peak or outlet was obtained from a $5 \times 10^4$ purified outlet to a 0.05 molar outlet peak by reversing the polarity of the leads 28 and 30 for about 5 seconds. The flow rates may vary; however in purification experiments with sodium chloride, the flow rates vary from 0.23 ml per minute to 3 ml per minute or more.

Figure 8:
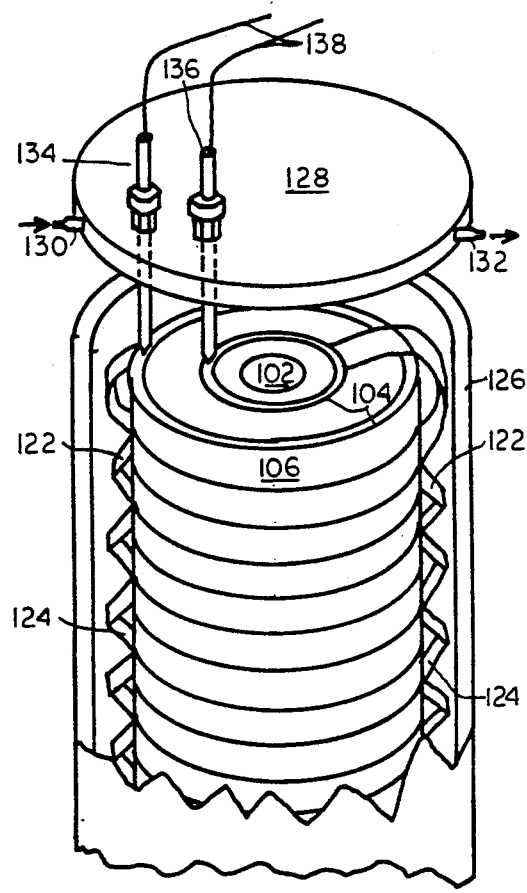
FIG. 8 is a fragmentary, schematic illustration of a controlled charge chromatographic apparatus of the invention with the flow-through capacitor of FIG. 5.

FIG. 5 shows a stacked washer flow-through capacitor 100 in an exploded form having a rubber washer 102 at the top end thereof to form a watertight seal when the capacitor 100 is put inside a standard filter cartridge holder 126 (see FIG. 8). The cartridge 100 contains end caps 106 made of an inert, non-conductive material, such as for example a high density polypropylene resin, with the end caps threaded on the inside to screw onto threads 108 on the end of a central tube 110. The bottom end cap 106 is a solid cap to close up the bottom end of the tube 110. The top end cap includes two concentric circles of inert conductive material 104, such as for example, but not limited to, gold, gold foil, graphite or platinum series metals and the like. The central supporting tube 110 comprises a porous polyethylene tube, for example a 10-inch tube of porous plastic with a ⅛-inch outside diameter and ⅛-inch wall thickness. The central tube 110 acts as a supporting member to hold the ring-shaped or washer parts together and under compression when the end caps 106 are threadably screwed against the ends of the central tube 110. The porous plastic tube 110 allows for flow out of the middle of the tube to the top end. The tube could also include a solid, rod-like element with longitudinal, fluted sides to provide support for the washer elements and also provide for flow out of the tube. Employment of a central, plastic, porous, polyethylene tube has the added advantage of being also a microfilter, for example, of one to five microns or less, so as to filter out any fine material which may leach off a carbon disk or other washer materials. The cartridge 100 includes a plurality of washer materials in sequence to include a porous, non-conductive spacer material with pores, for example, a synthetic, fibrous material or other type of non-conductive spacer material, such as fiberglass or woven nylon.

Washer material 116 comprises any inert, conductive backing material, for example, a 5-mil thick Graphoil ® brand (Union Carbide graphite foil material) with multiple holes 119 perforated in it to provide for better liquid flow therethrough. This graphite foil material (also see FIG. 6) provides a pair of washer materials 116 connected with a connecting bridge 118 having an optional notch 114 to accommodate electrical communication to a conductive material. The conductive material 116 with the connecting tab 118 is placed at the top and bottom of a high surface area conductive washer material 120 with half the resistance to an average particle in the conductor 120 thereby providing a capacitor with less internal resistance, which is desirable, as it increases the speed with which the capacitor may be electrically charged, and therefore the allowable flow rate of the solution to be purified can be increased. The tab or arm 118 connecting the two halves of the backing material 116 provides for the connecting tab or arm 116 to be crimped to form tabs that extend outside of the completed assembled flow-through cartridge, which tabs can then be utilized to form conductive leads. In one preferred embodiment, the conductive leads having charge may be faced inwardly.

The washer material 120 comprises any high surface area conductive material. One example is the use of a KX Industries extruded, activated carbon tubes which are held together with a small amount of polypropylene binder. These tubes are extruded in tube shapes two inches overall diameter with an inner diameter which is widened to 1⅜ inches and cut into rings of about ⅛ inch thickness. Such high surface area conductive material 120 may also include activated carbon cloth full of activated carbon fibers, since the compression afforded by the stacked washer cartridge flow design would compress the loose material and allow it to become conductive by inner particle contact, thus allowing the choice of other inexpensive, conductive, high surface area conductive materials.

The conductive leads material 122, as shown on the right hand side of the exploded diagram in FIG. 5, includes folded tab 124 which can be made of any electrically conductive material, such as for example Graphoil ®, or may also be a wire suitably coated to protect it from the environment or a naked inner wire of gold or platinum, along with the electrically conductive material, could be attached to the arm 118 The conductive material as illustrated is shown in corrugated form. The flat tab section 124 is designed to lie on top of parts 120 or 116 to form an electrical contact under compression. As illustrated, an option notch 114 can be employed to accommodate thickness of the tab, while in many cases the other materials are compressible enough so this added notch need not be employed. The conductive leads 122 and tabs 124 short together the alternating layers composed of conducting layers 116 and 120 which are separated by the insulating spacer 112 to form alternating washer anodes and cathodes up and down the central tube 110.

Figure 7:
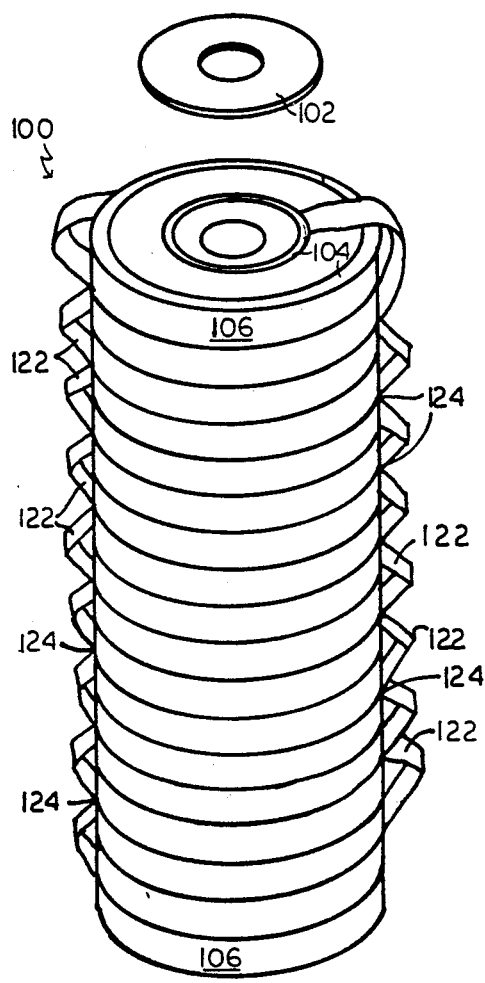
FIG. 7 is a perspective view of the assembled flow-through capacitor of FIG. 5.

FIG. 7 shows the assembled flow-through capacitor cartridge 100 showing the side leads 122 that short the alternating anode and cathode washer layers together in parallel. The tabs 124 are now pressed against the backing layers 116 to form electrical contact. The conductive leads 122 are also electrically connected on each of the conducting circles 104 in the end cap 106. The assembled flow-through capacitor cartridge 100 as illustrated in FIG. 7 is thus ready for insertion in a standard filter cartridge for use as a controlled charge chromatography system.

FIG. 8 is a fragmentary, partially sectional, schematic illustration of a controlled charge chromatography apparatus showing the use of the flow-through capacitor cartridge 100 within a standard filter cartridge 126 having a screw-on head 128 with the inlet 130 for the introduction of a liquid for a controlled charge chromatographic separation, and an outlet 132 for the removal of a purified liquid from the center of the central supporting tube 110. The cartridge head 128 is modified to allow watertight, electrically conductive leads 138 to an outside water power supply (not shown) with the employment of paired conductive rods, for example ⅜-inch graphite rods 134 and 136, having pointed ends, which are in electrical contact with the concentric circles 104 and the end caps 106 of the cartridge 100, with compression nuts used to form a watertight seal over the rods 134 and 136. Threaded inserts go in to the filter holder cartridge top 128 to corresponding threaded holes in the top cover for the employment of the rods 134 and 136 in a watertight fashion. The rods have leads 138 to a power supply (not shown by see FIG. 4). The filter holder top 128 is screwed tightly to form a watertight seal against washer 102. The conductive rods 134 and 136 are pressed firmly against the concentric conducting circles 104, thereby forming electrical contact through to the leads 122. Since the washers are concentric, no matter how the top is screwed on, the rods 134 and 136 will always be positioned in the right place against conductive circles 104.

In operation, a liquid to be purified is introduced through inlet 130, 130 flows to the outside within cartridge 126, and goes through from the inside to the outside of the washer 102. Purified fluid is then removed through the central tube 110 and therefore through outlet 132. While the conductive backing material has been described in a particular form, that is, two washers 116 with a conducting arm bridge 118, this particular form is not essential to the operation of the flow-through capacitor of the invention, and obviously may be replaced by other forms, but the illustrated form represents one preferred embodiment employing the electrically conductive backing material in the stacked washer flow-through capacitor of the invention.

Thus, as illustrated a new, improved and unique flow-through capacitor and controlled charge purification chromatography column system and method has been discovered which provides for the effective and rapid separation by a flow-through capacitor of high electric capacitance and high surface area, high adsorption ability, electrically conductive, stationary phase in the chromatographic column.

REFERENCES

[1] Bassler, Barbara and Hartwick, Richard, "Electrically Conductive Stationary Phases for HPLC", Abstract from AICHE Meeting, San Francisco, Calif., Nov. 5-10, 1989

[2] Antrim, Robert; Scherrer, Robert and Yacynych, Alexander, "Electrochromatography—A Preliminary Study of the Effect of Applied Potential On a Carbonaceous Chromatographic Column", *Anal. Chim. Acta.* 164 (1984) 283

[3] Blaedel, W. J. and Strohl, J. H., "Continuous Quantitative Electrolysis", *Anal. Chem.*, Vol. 36, No. 7, June, 1964

[4] Strohl, John and Polutanovich, Thomas, "A Packed Graphite Cell for Thin-Layer Chromatography", *Analytical Letters*, 2(8), pp. 423-431 (1969)

[5] Fujinaga, Taitiro, "Electrolytic Chromatography and Coulometric Detection With the Column Electrode", *Pure Applied Chemistry*, 25 (1971) pp. 709-726

[6] Hern, James and Strohl, John H., "Modified Graphites for Chelation and Ion Exchange", *Analytical Chemistry*, Vol. 50, No. Dec. 14, 1978

[7] Stoner, G. and Srinivasan, S., "Absorbtion of Blood Proteins on Metals Using Capacitance Techniques", *Journal of Physical Chemistry*, Vol. 74, No. 5, pp. 1088-1094, Mar. 5, 1970

[8] Newman, Arnold L., "Sintered Pellet with Biochemically Active Layer", U.S. Pat. No. 4,769,191, Sep. 6, 1988

[9] "KF for Electro Double Layer Capacitors", Toyobo Co. Bulletin, PCF 110

[10] Waldrop, M. Mitchell, *Science*, Vol. 247, No. 4939, Jan. 12, 1990, p. 161

I claim:

1. A flow-through capacitor for use in a chromatographic system for the purification of liquids containing materials which capacitor comprises:
   a) a central, longitudinal, electrically non-conductive support means to provide support for a plurality of washer elements thereon and to permit the longitudinal flow of a liquid toward the one or other end of the support means;
   b) a plurality of stacked washer elements arranged as a unit about the support means, the washer elements in each unit arranged in a close, contacting, sequential arrangement to include in each washer unit:
      i) a non-electrically conductive spacer washer element;
      ii) a high surface area, porous, electrically conductive washer element to act as a stationary phase of a chromatographic column, said washers being sized, dimensioned, and positioned to allow for placement into a chromatographic column; and
      iii) an electrically conductive backing washer element;
   c) means to electrically connect the alternating backing washer elements along the support means to form anode and cathode leads of the connected backing washer elements whereby anode and cathode washer elements are adapted to be connected to a power source to form the anode and cathode of the flow-through capacitor.

2. The capacitor of claim 1 wherein the support means comprises a central porous tube closed at one end and open at the other end for the receiving of purified liquid within the tube.

3. The capacitor of claim 2 wherein the central tube comprises a plastic tube having pores therein to act as an ultrafilter for the purified liquid.

4. The capacitor of claim 1 wherein the spacer washer element comprises a porous, fibrous, polymeric material.

5. The capacitor of claim 1 wherein the backing washer element comprises a conductive film layer selected from the group consisting of aluminum, tantalum and graphite.

6. The capacitor of claim 1 wherein the high surface area washer element is selected from the group consisting of compressed, activated carbon particles; activated carbon fibers; and electrodeposited platinum series black.

7. The capacitor of claim 6 wherein the high surface area washer element has a thickness of about 25 to 200 mils.

8. The capacitor of claim 1 wherein the backing washer has a plurality of holes therein to permit liquid flow therethrough.

9. The capacitor of claim 1 wherein the backing washer element comprises a pair of washer elements connected by an electrically conductive tab element.

10. The capacitor of claim 9 wherein the tab elements of attending washer elements are arranged on opposite sides of the support means.

11. The capacitor of claim 1 which includes means to electrically connect the anode and cathode washer elements.

12. The capacitor of claim 11 wherein the means to electrically connect comprises a pair of corrugated-type graphite foil elements electrically connected to the anode and cathode backing washer on opposite sides of the support means.

13. The capacitor of claim 1 wherein the support means includes threaded ends and includes a pair of end caps threadably secured to each end of the support means.

14. The capacitor of claim 13 which includes end caps, one end cap adapted to be secured to a top cover of a cartridge having spaced apart, concentric, electrically conductive materials, the electrically conductive material in the end cap electrically connected separately to the anode and cathode backing washer elements.

* * * * *